United States Patent [19]

Larsson

[11] Patent Number: 5,032,103
[45] Date of Patent: Jul. 16, 1991

[54] BREAST SHIELD

[75] Inventor: Karl O. A. H. Larsson, Zug, Switzerland

[73] Assignee: ISG/AG, Zug, Switzerland

[21] Appl. No.: 480,872

[22] Filed: Feb. 16, 1990

[51] Int. Cl.$^5$ ............................................. A41C 3/04
[52] U.S. Cl. ............................................ 450/37; 450/38; 128/890
[58] Field of Search .................. 450/36, 37, 38, 39, 450/40, 41, 47, 57, 63, 68, 72, 80, 81, 86, 87, 88; 128/155, 889, 890; 604/348, 896, 897

[56] References Cited

U.S. PATENT DOCUMENTS

| | | | |
|---|---|---|---|
| 16,396 | 1/1857 | Parker . | |
| 77,393 | 4/1868 | McLaughlin . | |
| 296,609 | 4/1884 | Pattee | 450/37 X |
| 406,491 | 7/1889 | Williams | 450/57 |
| 1,032,518 | 7/1912 | Thieringer . | |
| 1,082,198 | 12/1913 | Jencsa . | |
| 1,721,739 | 7/1929 | Kennedy | 450/39 X |
| 2,054,491 | 9/1936 | Tynan . | |
| 2,061,268 | 11/1936 | Becker | 450/39 |
| 2,345,649 | 4/1944 | Zimmerman et al. | 450/57 |
| 2,364,866 | 12/1944 | Meynier, Jr. . | |
| 2,448,938 | 9/1948 | Wayne | 604/346 OR |
| 2,495,307 | 1/1950 | Abramson | 604/346 X |
| 2,553,825 | 5/1951 | Langs | 450/81 |
| 2,579,365 | 12/1951 | Condé450 | 39/ |
| 2,630,119 | 3/1953 | Aagesen | 450/37 X |
| 2,659,085 | 11/1953 | Ericson | 450/39 |
| 2,748,771 | 6/1956 | Richards | 450/36 X |
| 2,864,373 | 12/1958 | Buckley | 450/57 |
| 2,891,544 | 6/1959 | London | 450/39 X |
| 2,896,623 | 7/1959 | Fitzgerald | 450/39 X |
| 3,176,686 | 4/1965 | Barnes | 450/39 X |
| 3,304,558 | 2/1967 | Mann | 450/57 X |
| 3,348,549 | 10/1967 | Brodman et al. | 450/57 |
| 3,513,852 | 5/1970 | Seidl | 450/36 |
| 3,532,096 | 10/1970 | Seidl | 450/36 X |
| 3,840,012 | 10/1974 | Rushton, Jr. | 450/37 X |
| 4,074,721 | 2/1979 | Smits et al. | 450/37 |
| 4,164,228 | 8/1979 | Weber-Unger | 450/37 |
| 4,172,002 | 10/1979 | Gluckin | 450/39 X |
| 4,195,639 | 4/1980 | Lee . | |
| 4,258,442 | 3/1981 | Eberl | 450/41 X |
| 4,270,538 | 6/1981 | Murphy | 450/37 X |
| 4,333,471 | 6/1982 | Nakai | 450/81 |
| 4,372,321 | 2/1983 | Robinson | 450/39 |
| 4,438,163 | 3/1984 | Anderson . | |
| 4,566,458 | 1/1986 | Weinberg . | |
| 4,754,750 | 7/1988 | Imonti | 450/81 X |
| 4,870,977 | 10/1989 | Imonti | 450/81 X |

FOREIGN PATENT DOCUMENTS

| | | | |
|---|---|---|---|
| 0022892 | 10/1955 | Fed. Rep. of Germany | 128/890 |
| 0969259 | 12/1950 | France | 450/39 |
| 1132335 | 3/1957 | France | 450/40 |
| 7772 | 4/1892 | United Kingdom . | |
| 1159117 | 7/1969 | United Kingdom | 450/81 |
| 2019722 | 11/1979 | United Kingdom | 450/41 |
| 2112288 | 7/1983 | United Kingdom | 450/39 |

OTHER PUBLICATIONS

Brochure Disclosing Breast Shells.

Primary Examiner—Werner H. Schroeder
Assistant Examiner—Jeanette E. Chapman
Attorney, Agent, or Firm—Willian Brinks Olds Hofer Gilson

[57] ABSTRACT

A breast shield is described having a dome-shaped shell with an open bottom and an elastic member that extends across the open bottom. The elastic member has an opening through which the breast nipple extends into the interior of the shell. The elastic member serves as a base or mount for the shell which resiliently spaces the shell from contacting the nipple. One embodiment of the shield aids in reinverting a nipple that is inverted.

14 Claims, 1 Drawing Sheet

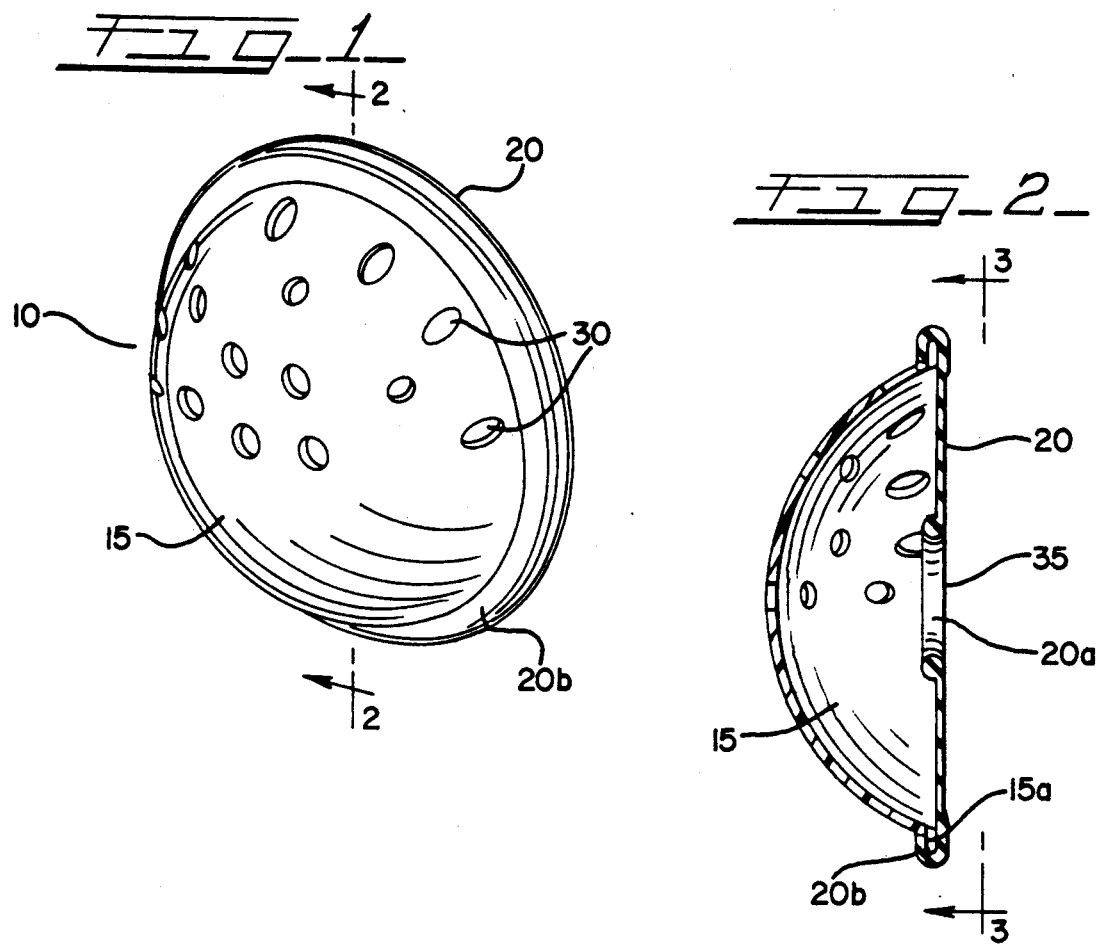

BREAST SHIELD

FIELD OF THE INVENTION

This invention relates generally to breast shields for nursing females, and more specifically to breast shields which protect the breast and nipple from irritation, and additionally, aid in reinverting a nipple that is inverted.

BACKGROUND OF THE INVENTION

It is not uncommon for women who are lactating to incur irritation of the breast and nipple areas. The nipples can become highly sensitized from nursing, and may crack or otherwise suffer any number of nursing-related topical problems. Chaffing of the breast or nipple area from clothing then becomes a concern. Aeration of the nipple area for certain conditions is also desirable.

Another problem associated with breast feeding is that some lactating women experience discomfort or are unable to breast feed because their nipples are inverted. Yet another problem is that breast milk may leak between nursing periods, staining overlying clothing.

It is thus quite desirable to protect the breasts and nipples of lactating women from the irritation or discomfort experienced from contact with clothing during the period they are nursing, and to aerate the nipples for certain conditions. It is also desirable to help those nursing females whose nipples are inverted to reinvert the nipple so they may be better able to breast feed. Protecting clothing from milk leakage is yet another desirable goal.

Products have been developed to prevent leakage of lacteal fluid that may stain clothing, or to prevent the breast and nipples of lactating females from coming in contact with outer garments that may cause chaffing or irritation. Aeration for the nipples is also provided by some devices.

For instance, U.S. Pat. No. 2,054,491 for a breast shield discloses a shield made of a semi-rigid cellulose material. The shield is placed directly against the breast, and an absorbant pad is secured in the lower portion of the shield to absorb any lacteal fluid that may leak from the breasts.

U.S. Pat. No. 2,748,771 shows a breast shield which is formed of a thin flexible material that is adapted to be placed inside the cup of a brassiere for collecting and retaining lacteal fluid. This shield encompasses the breast in intimate contact therewith, and uses a pad to absorb the milk.

Another device, U.S. Pat. No. 4,566,458 discloses a breast shield that protects the breast and nipple from external trauma. It directs the force of a blow along the rib cage of the wearer rather than on the breast itself. The shield closely encompasses the breast, and is formed from high impact absorbant material.

None of these previously used breast shields, however, provide for a shield that resiliently spaces the shield from the nipple area so that it does not contact the nipple. Rather, these breast shields enclose the breast and are in intimate contact therewith. This direct contact of the shields on the breasts, and on the nipples, in particular, can itself cause chaffing and irritation from the shields themselves. These prior art devices also do not apply a uniform pressure on the area of the breast surrounding the nipple to reinvert an inverted nipple.

SUMMARY OF THE INVENTION

The present invention is an improved breast shield for lactating women, in particular, which better protects the breast and nipple from irritation, and in one form also aids in reinverting inverted nipples.

More specifically, the breast shield of this invention comprises a dome-spaced shell that has an open bottom shaped to encompass a substantial portion of a woman's breast. The shield has an elastic member that extends across the open bottom of the shell. The elastic member, which is preferably a thin, almost membranous disk, contains an opening through which the nipple of the breast may extend into the shell. The elastic member forms a base for the shell, and is formed to resiliently space the shell from contact with the nipple. That is, the shell is resiliently supported on the breast by the elastic member, with the nipple extending into the shell but not in contact with the shell interior. Pressure applied to the shell to keep it in place, as by a brassiere or other clothing, is generally evenly distributed around the breast by the elastic member. A more comfortable breast shield is thereby also provided.

In one embodiment, the opening of the elastic member, in conjunction with the member's resiliency, is designed to aid in applying a uniform pressure on the breast around the nipple to reinvert an inverted nipple.

The invention, together with its attendant advantages, will be further understood by reference to the following detailed description taken in conjunction with the accompanying drawings, in which:

BRIEF DESCRIPTION OF THE DRAWINGS

FIG. 1 is a perspective view of a breast shield made in accordance with the present invention;

FIG. 2 is a cross-sectional view of the breast shield of FIG. 1 taken along line 2—2 of FIG. 1;

FIG. 3 is a rear view of the breast shield of FIG. 1 adapted for particular use with an inverted nipple; and FIG. 4 is a rear view of the breast shield of FIG. 1.

DETAILED DESCRIPTION OF EMBODIMENTS OF THE INVENTION

The breast shield 10 has a rigid hemispherical dome-shaped shell 15 and an elastic member 20. The shell 15 has an open bottom across which the elastic member 20 extends. Shell 15 is constructed from lightweight plastic. While a rigid hemispherical shell is disclosed, it could be semi-rigid or of a different shape.

The shell 15 is sized to encompass a substantial portion of a breast, and is intended to be centered about the nipple of the breast. The shell 15 may be worn within the cup of a nursing brassiere, or under other clothing. The upper portion (as worn) of the shell 15 is preferably perforated for ventilation and air flow by air holes 30. The diameter of the interior of the disclosed shell 15 is about 8.4 cm.

This embodiment of the present invention uses an elastic member 20 made of silicone. The elastic member 20 can, however, be constructed from any similar suitable flexible or elastic material. The elastic member 20 has an opening 35 centrally located therein through which the entire nipple of a breast extends into the interior of the shell 15. The opening 35 is about 2.3 cm. in diameter. As shown in FIG. 4, an enlarged opening 35' in another embodiment permits a surrounding portion of the breast to also extend through the opening 35. The enlarged opening 35' is about 4.6 cm. in diameter.

A ring-like bead 20a is formed around the openings 35 and 35' for comfort and added strength.

The elastic member 20 has a channel-shaped rim 20b formed about its perimeter. The rim 20b snaps over a radially extending lip 15a, which is formed around the open bottom of the shell 15. The elastic member 20 is sized to readily snap over the lip 15, pulling the member taut in the process. The member 20 is easily removed for cleaning.

The elastic member 20, when extended across the open bottom of the shell 15, serves as a base or mount for the shell 15 that resiliently spaces the shell 15 from directly contacting, e.g., resting on, the nipple of the breast. This protects the nipple of a lactating female from irritation from clothing as well as from the shell itself, and assures aeration of the nipple. The elastic member 20 conforms to a small extent to the shape of the breast when the shield is in place. The breast shield 10 is held in place by the pressure of the brassiere or other fitted garment.

The embodiment of the elastic member shown in FIGS. 2 and 3 has an opening 35 which closely surrounds the areola of the breast. The opening of the elastic member 20 permits substantially only the areola of the breast to extend into the shell's interior. In use, the taut elastic member 20 causes a generally uniform pressure to be exerted on the breast in the area closely surrounding the areola. This pressure serves to re-invert a nipple that is inverted, while also protecting the nipple from irritation in the manner described above.

Thus, while the invention has been described in connection with reference to specific exemplary embodiments, it will be apparent to those skilled in the art that various changes and modifications to the structure, arrangement, portions, elements, materials and components used in the practice of this invention are possible without departing from the principals of this invention.

What is claimed is:

1. A breast shield for a lactating woman, comprising:
   a dome-shaped shell having an open bottom sized to encompass a substantial portion of the breast centered on the nipple, and
   an elastic member extending across said open bottom, said elastic member having an opening defined therein through which the nipple extends into said shell, said elastic member resiliently spacing said shell from the nipple.

2. A breast shield for protecting a breast nipple from irritation comprising:
   a rigid dome-shaped shell having an interior with an open bottom sized to encompass a substantial portion of the breast centered on the nipple, and
   an elastic generally planar mounting member which extends across said open bottom, said mounting member having an opening defined therein through which the entire nipple extends into said shell interior, said mounting member being received on said shell and drawn taut to form a support surface for said shell on the breast which resiliently spaces said shell from the nipple.

3. The breast shield of claim 2 wherein said opening closely surrounds the areola, said mounting member having a tautness sufficient to exert a pressure on the breast adjacent said opening to re-invert an inverted nipple.

4. A breast shield for a lactating woman, comprising:
   a dome-shaped shell having an open bottom sized to encompass a substantial portion of the breast centered on the nipple, and
   elastic means extending across said open bottom and having an opening defined therein through which a breast nipple may extend, said elastic means resiliently mounting said shell on the breast and spacing said shell from the nipple.

5. The breast shield of claim 4 wherein said elastic means is a generally planar elastic member having a central opening through which the nipple extends into said shell.

6. A breast shield for a lactating woman having inverted nipples, comprising:
   a dome-shaped shell having an open bottom sized to encompass a substantial portion of the breast centered on the nipple; and
   elastic means extending across said open bottom and generally conforming to the shape of the breast for resiliently mounting said shell on the breast with the nipple extending through an opening defined in said elastic means, which opening closely surrounds the areola, said elastic means spacing said shell from the nipple and applying a generally uniform pressure on the breast in the area of the areola to re-invert an inverted nipple.

7. The breast shield of claim 6 wherein said elastic means is a planar elastic member having a central opening through which the nipple extends into said shell.

8. A breast shield for protecting the nipple of a lactating woman from irritation, comprising:
   a rigid hemispherical dome-shaped shell having an interior and a radially extending lip surrounding an open bottom sized to encompass a substantial portion of the breast centered on the nipple, with a plurality of ventilation holes provided through said shell communicating with said interior; and
   an elastic generally planar disk-shaped member received on said lip and stretched taut across said open bottom, said elastic member having an opening defined therein through which the entire nipple extends into said shell interior, said elastic member generally deforming to the shape of the breast when said shield is emplaced and under pressure from overlying clothing, and further forming a taut support surface for said shell on the breast and resiliently spacing said shell from contact with the nipple.

9. A breast shield for a lactating woman comprising:
   a first member formed of a rigid material shaped to encompass a human breast, said first member having an open rearward portion; and
   a second member formed of an elastic material extending across said open rearward portion and having an opening defined therein through which at least a nipple of the breast projects, said second member overlying and contacting the breast and resiliently spacing the breast nipple from making contact with said first member.

10. The breast shield of claim 9 wherein said first member is a substantially dome-shaped shell.

11. A breast shield for a lactating woman, comprising:
    a rigid dome-shaped shell having an open rearward portion and shaped to encompass a substantial portion of a human breast, and
    a taut elastic member extending across said open rearward portion and having a centrally located opening defined therein through which an entire nipple of a breast may project, said elastic member forming an interior cavity with said dome-shaped shell when extended across the open rearward portion of said shell and resiliently spacing said shell from contact with the nipple.

12. The breast shield of claim 11 wherein said elastic member opening closely surrounds the areola and exerts a uniform pressure on an area of the breast adjacent to said opening to reinvert an inverted nipple.

13. A breast shield for protecting the nipple of a lactating woman from irritation from clothing, comprising:
   a rigid hemispherical dome-shaped shell having a plurality of air vents formed therethrough, an open rearward portion and a lip formed about the circumference of said open rearward portion, said shell being shaped to overlie a substantial portion of a breast, and
   a thin elastic disk-shaped member which extends across said open rearward portion of said shell and forms an interior cavity with said shell, said elastic member having an opening centrally located therein which is sized to receive an entire nipple of a breast therethrough, said elastic member having a peripheral channel-shaped rim which is removably received on said shell lip in a snap fit with said elastic member thereby being drawn taut across said rearward portion and forming a base for said shell, and which resiliently spaces said shell from contact with the nipple when the nipple extends into said interior cavity.

14. The breast shield of claim 13 wherein said elastic member opening closely surrounds the areola of the breast and applies a generally uniform pressure on the area adjacent to the areola to re-invert an inverted nipple.

* * * * *